(12) United States Patent
Hashimoto et al.

(10) Patent No.: US 10,905,508 B2
(45) Date of Patent: Feb. 2, 2021

(54) REMOTE CONTROL ROBOT SYSTEM

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 268 days.

(21) Appl. No.: 15/755,201

(22) PCT Filed: May 27, 2016

(86) PCT No.: PCT/JP2016/002586
§ 371 (c)(1),
(2) Date: Feb. 26, 2018

(87) PCT Pub. No.: WO2017/033359
PCT Pub. Date: Mar. 2, 2017

(65) Prior Publication Data
US 2018/0243915 A1    Aug. 30, 2018

(30) Foreign Application Priority Data

Aug. 25, 2015  (JP) .................................. 2015-165479

(51) Int. Cl.
*B25J 9/16* (2006.01)
*B25J 13/00* (2006.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ... B25J 3/00; B25J 9/1664; B25J 13/08; B25J 3/04; B25J 11/008; B25J 13/085;
(Continued)

(56) References Cited

U.S. PATENT DOCUMENTS 5,182,641 A * 1/1993 Diner ..................... H04N 7/181
                                                     348/113
5,331,413 A * 7/1994 Diner ..................... H04N 7/181
                                                     348/114
(Continued)

FOREIGN PATENT DOCUMENTS

| CN | 102169348 A | 8/2011 |
| JP | S60-217781 A | 10/1985 |

(Continued)

OTHER PUBLICATIONS

Aug. 2, 2016 International Search Report issued in International Patent Application No. PCT/JP2016/002586.
(Continued)

*Primary Examiner* — Stephen Holwerda
(74) *Attorney, Agent, or Firm* — Oliff PLC (57) ABSTRACT

A remote control robot system is provided, which includes robotic arm configured to perform a given work, remote control device for an operator to remotely manipulate operation of robotic arm, plurality of cameras configured to image the work of robotic arm, monitor configured to display a captured image that is sent, camera selecting device configured to generate, in response to receiving an operator's selection of one camera from the plurality of cameras, camera selection information for switching captured image displayed on monitor to captured image from selected camera, storage device configured to store information where operational information related to operation of robotic arm in work is associated with camera selection information, as automatic switching information, and an image processor
(Continued)

configured to send to monitor the captured image from camera selected from plurality of cameras based on automatic switching information stored in storage device.

4 Claims, 3 Drawing Sheets

(51) Int. Cl.
| | |
|---|---|
| G05B 19/418 | (2006.01) |
| H04N 5/232 | (2006.01) |
| H04N 7/18 | (2006.01) |
| A61B 34/37 | (2016.01) |
| B25J 9/00 | (2006.01) |
| B23P 19/04 | (2006.01) |
| B25J 19/04 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 9/1674; B25J 13/003; B25J 13/088; B25J 9/1628; B25J 9/1689; B25J 13/065; B25J 9/1682; B25J 19/04; B25J 9/0087; B25J 13/00; B25J 9/0081; B25J 13/084; B25J 9/161; B25J 13/006; B25J 13/087; B25J 9/0084; B25J 9/1653; B25J 9/163; B25J 13/02; B25J 19/023; B25J 9/1697; B25J 13/025; B25J 19/028; B25J 9/1669; B25J 9/1602; B25J 9/1646; B25J 13/06; B25J 18/00; B25J 9/1633; B25J 9/1612; H04N 5/23219; H04N 7/181; G05B 19/4182; A61B 34/37; A61B 34/32; B23P 19/04; G06F 3/017; G06T 7/62; G06T 7/70; B23Q 15/12
See application file for complete search history.

(56) References Cited

U.S. PATENT DOCUMENTS

| | | | | |
|---|---|---|---|---|
| 5,689,619 | A * | 11/1997 | Smyth | G02B 27/0093 706/45 |
| 2010/0118141 | A1* | 5/2010 | Bouchon-Meunier | H04N 5/232 348/135 |
| 2010/0185990 | A1 | 7/2010 | Ha et al. | |
| 2011/0199487 | A1* | 8/2011 | Husoy | G05B 19/418 348/159 |
| 2012/0294696 | A1 | 11/2012 | Summer et al. | |

FOREIGN PATENT DOCUMENTS

| | | |
|---|---|---|
| JP | H06-250730 A | 9/1994 |
| JP | H10-249786 A | 9/1998 |
| JP | 2003-311661 A | 11/2003 |
| JP | 3924495 B2 | 6/2007 |
| JP | 2011-158981 A | 8/2011 |
| KR | 10-2010-0085297 A | 7/2010 |

OTHER PUBLICATIONS

Jun. 6, 2017 Office Action issued in Taiwanese Patent Application No. 105126540.
English translation of Jun. 24, 2020 Search Report issued in Chinese Patent Application No. 2016800487113.

* cited by examiner

REMOTE CONTROL ROBOT SYSTEM

TECHNICAL FIELD

The present disclosure relates to a remote control robot system.

BACKGROUND ART

Conventionally, industrial robots are used for an iterative work, such as an assembling work of a component. The industrial robot is capable of automatically performing a taught operation at high speed and with sufficient accuracy by being taught information required for the work. However, when performing a work requiring a delicate positioning or a work environment is changed, it may be advantageous that an operator performs the work by remotely manipulating the robot, rather than the robot performs the work automatically. Patent Document 1 proposes a remote control robot system which is capable of operating a robot based on manipulating instructions from the operator.

The remote control robot system disclosed in Patent Document 1 includes a camera which images a work environment, and a display device which displays a captured image which is imaged by the camera, and it is configured so that, before performing a work which is difficult to be automated, the robotic arm is switched from an automatic operation to a manual operation. The operator remotely manipulates the robotic arm while looking at the captured image displayed on the display device to cause the robotic arm to perform a given work.

In such a remote control robot system, if only one camera which images the work environment is provided, the operator is not able to grasp a spatial relationship between a work object and the robot only in one direction. Thus, it is difficult for the operator to manipulate the robotic arm and cause the robotic arm to perform the work with sufficient accuracy. Patent Document 1 describes that the system is comprised of a plurality of cameras, and the camera from which the captured image to be displayed on the display device is taken is switched therebetween.

REFERENCE DOCUMENT OF CONVENTIONAL ART

Patent Document

[Patent Document 1] JP3924495B2

DESCRIPTION OF THE DISCLOSURE

Problems to be Solved by the Disclosure

When the remote control robot system is comprised of the plurality of cameras, it is necessary to adjust beforehand a timing of switching the camera before the work so that the operator is able to accurately grasp the spatial relationship between the work object and the robot, while looking at the display device. This adjustment is troublesome for the operator, and when a change occurs in the work object etc., a readjustment needs to be performed. Thus, although the burden of the adjustment of the switching timing of the camera is desirably reduced, nothing regarding this aspect is described in Patent Document 1.

Therefore, one purpose of the present disclosure is to provide a remote control robot system capable of easily switching a camera which displays on a monitor an image suitable for remotely manipulating a robotic arm.

SUMMARY OF THE DISCLOSURE

According to one aspect of the present disclosure, a remote control robot system is provided, which includes a robotic arm configured to perform a given work, a remote control device for an operator to remotely manipulate operation of the robotic arm, a plurality of cameras configured to image the work of the robotic arm, a monitor configured to display a captured image that is sent, a camera selecting device configured to generate, in response to receiving an operator's selection of one camera from the plurality of cameras, camera selection information for switching the captured image displayed on the monitor to the captured image from the selected camera, a storage device configured to store information where operational information related to operation of the robotic arm in the work is associated with the camera selection information, as automatic switching information, and an image processor configured to send to the monitor the captured image from the camera selected from the plurality of cameras based on the automatic switching information stored in the storage device.

With the above configuration, one camera among the plurality of cameras is selected by the camera selecting device and the captured image displayed on the monitor is switched. Moreover, the information where the operational information related to the operation of the robotic arm in the work is associated with the camera selection information is stored in the storage device as the automatic switching information. Thus, in the subsequent works of the robotic arm, even if the camera selection is not made by the camera selecting device, the image processor is capable of automatically switching the captured image displayed on the monitor based on the automatic switching information stored in the storage device so that the captured image is suitable for remotely manipulating the robotic arm. Further, since the automatic switching information is storable in actual work by performing camera switching by using the camera selecting device, the timing of automatically switching the camera can be adjusted in the real work even if the timing of the camera switching is not preadjusted before the work.

The remote control robot system described above may further include a switching mode selecting part configured to receive an operator's selection of one of a camera selecting mode in which the captured image from the camera selected based on the camera selection information sent from the camera selecting device is sent to the monitor, and an automatic switching mode in which the captured image from the camera selected based on the automatic switching information stored in the storage device is sent to the monitor, as a processing mode of the image processor. With this configuration, it can be selected by the switching mode selecting part whether the captured image displayed on the monitor is switched by the operator's selection, or switched automatically. Thus, the operator is able to change the method of switching the camera flexibly according to the contents of work, the work object, etc.

The remote control robot system described above may include a plurality of sub-monitors, different from the monitor, provided corresponding to the plurality of cameras, respectively, and configured to display the captured images from the corresponding cameras among the plurality of cameras. The camera selecting device may sense an operator's line-of-sight to identify the sub-monitor among the plurality of sub-monitors, to which the operator's line-of-sight is directed for a given period of time, and may accept the camera corresponding to the identified sub-monitor as the camera selected by the operator. With this configuration, the selection of the camera for switching the image of the monitor can be performed without using hands.

Effect of the Disclosure

The present disclosure can provide the remote control robot system capable of easily switching the camera which displays on the monitor the image suitable for remotely manipulating the robotic arm.

MODES FOR CARRYING OUT THE DISCLOSURE

First Embodiment

Hereinafter, a remote control robot system according to a first embodiment of the present disclosure is described with reference to the accompanying drawings. The robot system 100 according to this embodiment is a system including a robotic arm 1 which repeatedly perform a given work, and a remote control device 2 which remotely manipulates the robotic arm 1 by manual operation. In the robot system 100, an operator who is located at a position distant from a workspace of the robotic arm 1 (outside of the workspace) is able to manually operate or manipulate the remote control device 2 to input instructions so that the robotic arm 1 performs operation corresponding to the instructions to perform a specific work. In addition, in the robot system 100, the robotic arm 1 is also capable of automatically performing the given work without the operator manipulating the remote control device 2.

An operating mode in which the robotic arm 1 is operated according to the instructions inputted through the remote control device 2 is herein referred to as a "manual mode." Note that the "manual mode" also includes a case in which part of the operation of the robotic arm 1 under operation is automatically corrected based on instructions inputted by the operator manipulating the remote control device 2. Moreover, an operating mode in which the robotic arm 1 is operated according to a preset task program is referred to as an "automatic mode."

Further, the robot system 100 of this embodiment is configured so that operation to be performed automatically is correctable by reflecting the manipulation of the remote control device 2 in the automatic operation of the robotic arm 1 while the robotic arm 1 is operating automatically. An operating mode in which the robotic arm 1 is operated according to the preset task program while the instructions inputted through the remote control device 2 is reflectable is herein referred to as a "correctable automatic mode." Note that the "automatic mode" described above is distinguished from the "correctable automatic mode" in that the manipulation of the remote control device 2 is not reflected in the operation of the robotic arm 1 when the operating mode in which the robotic arm 1 is operated is the automatic mode.

Figure 1:
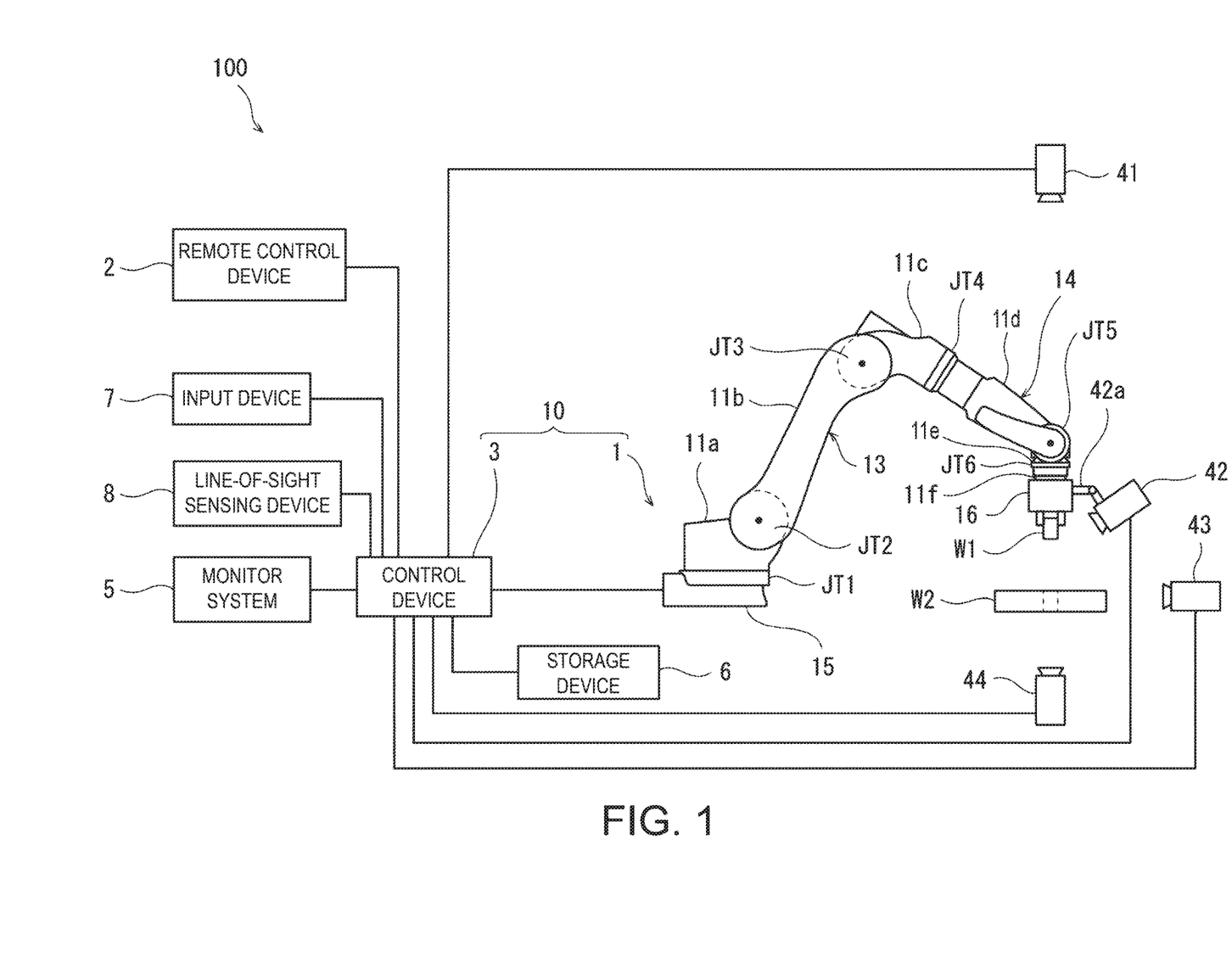
FIG. 1 is a schematic diagram illustrating a configuration of a remote control robot system according to a first embodiment.

First, with reference to FIG. 1, a configuration of the robot system 100 according to this embodiment is described. FIG. 1 is a schematic diagram illustrating one example of the configuration of the robot system 100 according to this embodiment. As illustrated in FIG. 1, the robot system 100 includes an industrial robot 10, the remote control device 2, a camera system 4, a monitor system 5, a storage device 6, an input device 7, and a line-of-sight sensing device 8. Below, each component of the robot system 100 is described in detail.

(Structure of Industrial Robot 10)

The industrial robot 10 includes the robotic arm 1, an end effector 16 attached to a tip end of the robotic arm 1, and a control device 3 which governs operations of the robotic arm 1 and the end effector 16. In this embodiment, the industrial robot 10 is a robot which performs an assembling work in which an assembling object W1 is assembled to an assembled object W2. More specifically, the assembled object W2 is supported by a support table (not illustrated), and has a hole penetrating in the vertical direction to assemble the assembling object W1. The end effector 16 is a grip part which grips the assembling object W1. Note that the industrial robot 10 is not limited in particular, and for example, it may be a welding robot, a painting robot, an application robot, an inspection robot, etc.

The robotic arm 1 includes a pedestal 15, an arm part 13 supported by the pedestal 15, and a wrist part 14 which is supported by a tip end of the arm part 13 and to which the end effector 16 is attached. As illustrated in FIG. 1, the robotic arm 1 is an articulated robotic arm having a plurality of (three or more) joints JT1-JT6, which is constructed by serially coupling a plurality of links 11a-11f. In more detail, at the first joint JT1, the pedestal 15 and a base-end part of the first link 11a are coupled to each other so as to be rotatable about an axis extending vertically. At the second joint JT2, a tip-end part of the first link 11a and a base-end part of the second link 11b are coupled to each other so as to be rotatable about an axis extending horizontally. At the third joint JT3, a tip-end part of the second link 11b and a base-end part of the third link 11c are coupled to each other so as to be rotatable about an axis extending horizontally. At the fourth joint JT4, a tip-end part of the third link 11c and a base-end part of the fourth link 11d are coupled to each other so as to be rotatable about an axis extending in the longitudinal directions of the fourth link 11c. At the fifth joint JT5, a tip-end part of the fourth link 11d and a base-end part of the fifth link 11e are coupled to each other so as to be rotatable about an axis perpendicular to the longitudinal directions of the link 11d. At the sixth joint JT6, a tip-end part of the fifth link 11e and a base-end part of the sixth link 11f are twistably and rotatably coupled to each other. In addition, a mechanical interface is provided to a tip-end part of the sixth link 11f. The end effector (the grip part in this embodiment) 16 corresponding to the contents of work for the work objects (the assembling object W1 and the assembled object W2 in this embodiment) is attached to the mechanical interface attachably and detachably.

The arm part 13 of the robotic arm 1 is formed by a coupled body of the links and the joints comprised of the first joint JT1, the first link 11a, the second joint JT2, the second link 11b, the third joint JT3, and the third link 11c, described above. Moreover, the wrist part 14 of the robotic arm 1 is formed by a coupled body of the links and the joints comprised of the fourth joint JT4, the fourth link 11d, the fifth joint JT5, the fifth link 11e, the sixth joint JT6, and the fourth link 11f, described above.

The joints JT1-JT6 are each provided with a drive motor (not illustrated) as one example of an actuator which relatively rotates two members connected by the joint. The drive motor is, for example, a servo motor which is servo-controlled by the control device 3. Moreover, the joints JT1-JT6 are each provided with a rotation sensor (not illustrated) which senses a rotational position of the drive motor, and a current sensor (not illustrated) which senses current for controlling the rotation of the drive motor. The rotation sensor is, for example, an encoder.

The control device 3 is comprised of, for example, an arithmetic part (not illustrated), such as a micro controller, an MPU, a PLC (Programmable Logic Controller), or a logic circuit, and a memory part (not illustrated), such as a ROM or a RAM.

Figure 2:
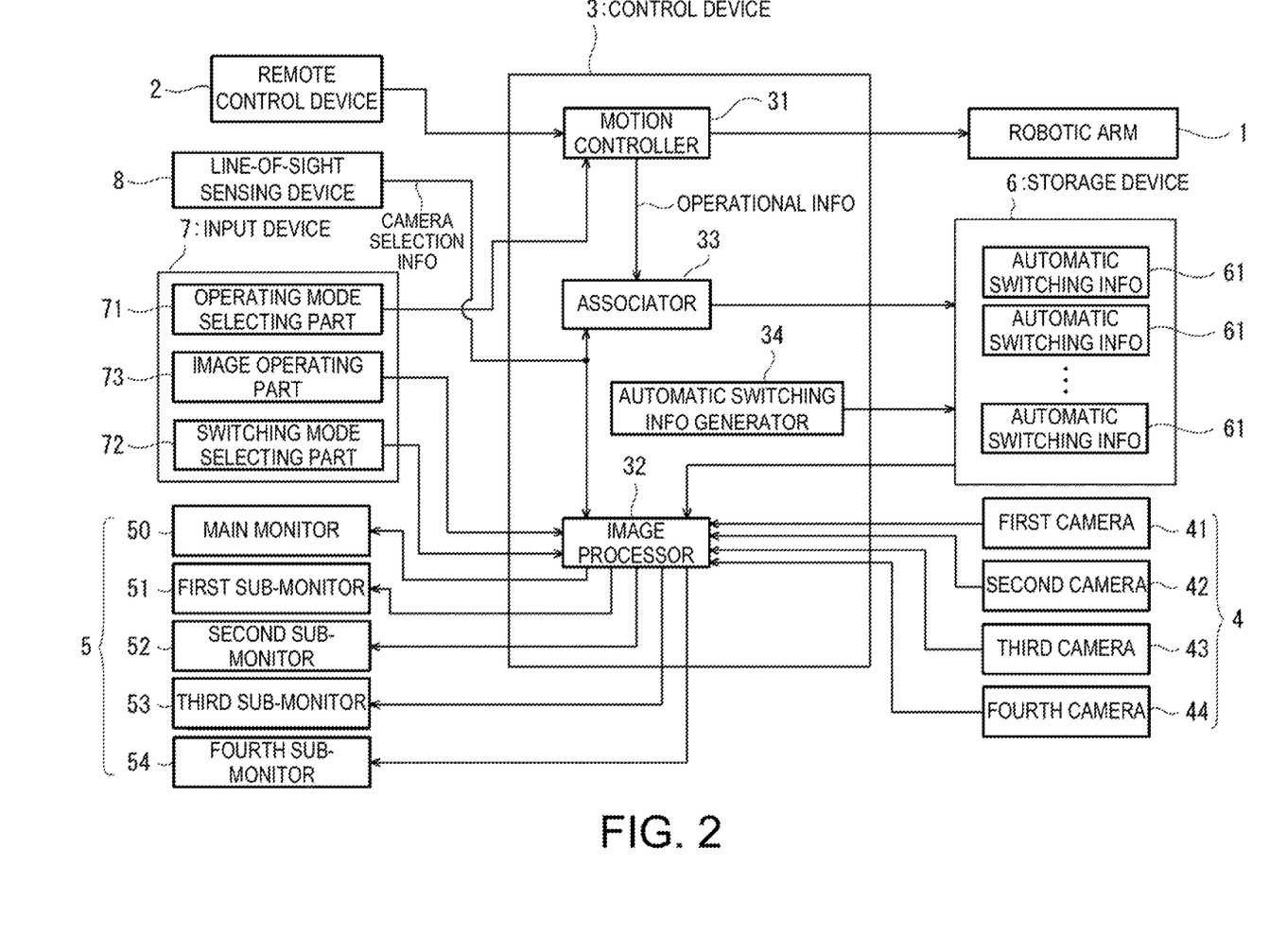
FIG. 2 is a schematic diagram illustrating a configuration of a control system of the remote control robot system illustrated in FIG. 1.

FIG. 2 is a schematic diagram illustrating a configuration of a control system of the robot system 100. As illustrated in FIG. 2, the control device 3 includes a motion controller 31, an image processor 32, an associator 33, and an automatic switching information generator 34, as functional blocks. The functional blocks provided to the control device 3 are implementable, for example, by the arithmetic part of the control device 3 reading and executing the program stored in the memory part. Details of each of the functional blocks 31-34 are described later.

(Remote Control Device 2)

Returning to FIG. 1, the remote control device 2 is a device which receives a manipulating instruction from the operator. The remote control device 2 is installed outside the workspace of the robotic arm 1. The remote control device 2 in this embodiment is, for example, a joystick. Manipulating information is generated by manipulating the remote control device 2, and the generated manipulating information is sent to the control device 3. In the robot system 100 of this embodiment, when the manipulating information is sent to the control device 3 while the operating mode in which the robotic arm 1 is operated is the manual mode, the robotic arm 1 performs operation according to the manipulating information. Moreover, when the manipulating information is sent to the control device 3 while the operating mode in which the robotic arm 1 is operated is the correctable automatic mode, the operation of the robotic arm 1 which is operating automatically is corrected using the manipulating information.

(Camera System 4)

The camera system 4 is comprised of a first camera 41, a second camera 42, a third camera 43, and a fourth camera 44. The first camera 41, the second camera 42, the third camera 43, and the fourth camera 44 are installed in a space where the robotic arm 1 is provided, and they image a work of the robotic arm 1 from different directions. Specifically, the first camera 41 is disposed above the supported assembled object W2 and the robotic arm 1, and entirely images the assembled object W2 and the robotic arm 1 from above. The second camera 42 is attached to a tip end of a support arm 42a fixed to the end effector 16, and is disposed so that a field of view of the second camera 42 includes a tip-end portion of the end effector 16 (i.e., a part which grips the assembling object W1). That is, when the end effector 16 grips the assembling object W1, the second camera 42 images the assembling object W1, as well as the tip-end portion of the end effector 16. The third camera 43 is provided so as to image the assembled object W2 supported by the support table from sideway. The fourth camera 44 is provided so as to image the assembled object W2 supported by the support table from below. For example, the assembled object W2 is provided so that the extending direction of the hole aligns with the extending direction of the optical axis of the fourth camera 44.

The first camera 41, the second camera 42, the third camera 43, and the fourth camera 44 are connected to the control device 3 wiredly or wirelessly, respectively, and captured images which are imaged by the cameras 41-44 are sent to the image processor 32 of the control device 3, respectively.

(Monitor System 5)

The monitor system 5 is comprised of a main monitor 50, a first sub-monitor 51, a second sub-monitor 52, a third sub-monitor 53, and a fourth sub-monitor 54. The main monitor 50 and the first to fourth sub-monitors 51-54 are connected to the control device 3 wiredly or wirelessly, respectively, and the captured images sent from the control device 3 are displayed on the respective monitors 50-54. The screen size of the main monitor 50 is larger than those of the first to fourth sub-monitors 51-54, and the operator (operator) manipulates the remote control device 2 while looking at the captured image outputted to the main monitor 50. The captured image from a camera which is selected by the image processor 32 is sent to the main monitor 50.

The first to fourth sub-monitors 51-54 are monitors provided corresponding to the first to fourth cameras 41-44, respectively. The captured images from the corresponding cameras are displayed on the first to fourth sub-monitors 51-54, respectively. That is, the captured image from the first camera 41 is displayed on the corresponding first sub-monitor 51, the captured image from the second camera 42 is displayed on the corresponding second sub-monitor 52, the captured image from the third camera 43 is displayed on the corresponding third sub-monitor 53, and the captured image from the fourth camera 44 is displayed on the corresponding fourth sub-monitor 54. In this embodiment, although the captured images imaged by the first to fourth cameras 41-44 are sent to the first to fourth sub-monitors 51-54 through the control device 3, respectively, the captured images imaged by the first to fourth cameras 41-44 may be sent to the first to fourth sub-monitors 51-54 directly or through another device, respectively.

(Line-of-Sight Sensing Device 8)

The line-of-sight sensing device 8 is a device which senses a line-of-sight of the operator. In this embodiment, the line-of-sight sensing device 8 functions as a camera selecting device of the present disclosure which receives a selection of one camera from the first to fourth cameras 41-44 by the operator. That is, the line-of-sight sensing device 8 is used by the operator to select which captured image imaged by any one of the first to fourth cameras 41-44 is to be displayed on the main monitor 50.

The line-of-sight sensing device 8 senses to which monitor among the first to fourth sub-monitors 51-54 the line-of-sight of the operator who manipulates the remote control device 2 is directed, and identifies the sub-monitor to which the operator's line-of-sight is directed. Then, the line-of-sight sensing device 8 accepts the camera corresponding to the identified sub-monitor as a camera selected by the operator. For example, the line-of-sight sensing device 8 determines whether the operator's line-of-sight is directed for a given period of time to one certain sub-monitor, and when determined that the line-of-sight is directed for the given period of time, it accepts this sub-monitor as the camera selected by the operator.

The line-of-sight sensing device 8 generates camera selection information by accepting the selection of the camera by the operator's line-of-sight. The camera selection information is information for switching the captured image displayed on the main monitor 50 to the captured image from the selected camera. The line-of-sight sensing device 8 is connected to the control device 3 wiredly or wirelessly, and the generated camera selection information is sent to the image processor 32 and the associator 33 of the control device 3. In this embodiment, the line-of-sight sensing device 8 may be a mountable type in which it is mountable to the operator, or may be a non-mountable type.

(Input Device 7)

The input device 7 is an input device which receives the manipulating instruction from the operator and inputs the received manipulating instruction into the control device 3. The input device 7 is installed outside the workspace, together with the remote control device 2. In this embodiment, the input device 7 is a tablet terminal. Note that the configuration of the input device 7 is not limited in particular, and for example, it may be a switch, an adjustment knob, a control lever, a personal computer, or the like. As illustrated in FIG. 2, the input device 7 includes an operating mode selecting part 71, a switching mode selecting part 72, and an image operating part 73. In this embodiment, the operating mode selecting part 71, the switching mode selecting part 72, and the image operating part 73 are configured by respective operating buttons etc. on a display screen of the tablet terminal.

The operating mode selecting part 71 is used for the operator to select the operating mode in which the robotic arm 1 is operated, from the automatic mode, the correctable automatic mode, and the manual mode, which are described above. Information related to the operating mode selected by the operating mode selecting part 71 is sent to the motion controller 31 of the control device 3. The motion controller 31 operates the robotic arm 1 based on the information sent from the operating mode selecting part 71, i.e., according to the operating mode selected by the operating mode selecting part 71.

Specifically, the manipulating information generated by manipulating the remote control device 2 is sent to the motion controller 31. Moreover, the memory part of the control device 3 stores scheduled route information for operating the robotic arm 1 automatically, and the scheduled route information is sent to the motion controller 31. The motion controller 31 uses one or both of the scheduled route information and the manipulating information according to the operating mode selected by the operating mode selecting part 71.

When the operating mode selected by the operating mode selecting part 71 is the manual mode, the motion controller 31 uses the manipulating information. In more detail, when the operating mode in which the robotic arm 1 is operated is the manual mode, the motion controller 31 controls the operation of the robotic arm 1 by using the manipulating information (inputted instructions) sent by manipulating the remote control device 2, without using the scheduled route information.

Moreover, when the operating mode selected by the operating mode selecting part 71 is the automatic mode, the motion controller 31 uses the scheduled route information. In more detail, when the operating mode in which the robotic arm 1 is operated is the automatic mode, the motion controller 31 controls the operation of the robotic arm 1 by using the scheduled route information according to the preset task program, without using the manipulating information sent from the remote control device 2.

Moreover, when the operating mode selected by the operating mode selecting part 71 is the correctable automatic mode, the motion controller 31 uses both the scheduled route information and the manipulating information. Note that, when the operating mode is the correctable automatic mode and the manipulating information is not sent to the motion controller 31, the motion controller 31 uses only the scheduled route information. In more detail, when the operating mode in which the robotic arm 1 is operated is the correctable automatic mode, the motion controller 31 uses both the scheduled route information and the manipulating information to control the operation of the robotic arm 1 when the manipulating information is received while the robotic arm 1 is operating automatically using the scheduled route information. Thus, the scheduled route to be automatically traced by the robotic arm 1 based on the scheduled route information is corrected.

The switching mode selecting part 72 is used, in the work of the robotic arm 1, in order for the operator to select whether the captured image displayed on the main monitor 50 is switched automatically or switched by the operator's selection. The switching mode selecting part 72 receives the selection of either one of the camera selecting mode and the automatic switching mode from the operator, as a processing mode of the image processor 32. The camera selecting mode is a processing mode in which the image processor 32 switches the captured image displayed on the main monitor 50 based on the camera selection information sent from the line-of-sight sensing device 8. Moreover, the automatic switching mode is a processing mode in which the image processor 32 switches the captured image displayed on the main monitor 50 based on the automatic switching information stored in the storage device 6.

The image operating part 73 is used in order for the operator to operate the captured image displayed on the main monitor 50. For example, the image operating part 73 may be configured so that the captured image displayed on the main monitor 50 is enlargeable and shrinkable.

(Storage Device 6)

The storage device 6 is a readable and writable recording medium, and stores automatic switching information 61 which is information for automatically switching the captured image displayed on the main monitor 50. The automatic switching information 61 is generated by the associator 33 of the control device 3.

The associator 33 associates the camera selection information sent from the line-of-sight sensing device 8 with information related to the operation of the robotic arm 1 for one work (hereinafter, referred to as "the operational information") to generate the automatic switching information.

Here, the operational information is, for example, positional information on the tip-end part of the robotic arm 1, posture information on the robotic arm 1, situation information on the end effector 16, or a combination of these. The positional information and the posture information described above are, for example, calculated from the rotational positional information on each drive motor sent from the rotation sensor of the robotic arm 1. The situation information on the end effector 16 is information, for example, when the end effector 16 is the grip part, related to whether the grip part is in the state of gripping the work object. In this embodiment, the operational information is sent from the motion controller 31 to the associator 33.

The automatic switching information 61 is information for automatically switching without camera selection of the operator by the line-of-sight sensing device 8 the captured image displayed on the main monitor 50 in the subsequent works of the robotic arm 1. By using the automatic switching information 61, the captured image displayed on the main monitor 50 is automatically switched at the same timing as the case where the captured image is switched by the operator's selection. Note that, in the work after the automatic switching information 61 is stored in the storage device 6, the automatic switching information 61 does not need to be used. For example, also in the work after the automatic switching information 61 is stored in the storage device 6, the captured image displayed on the main monitor 50 is switched by the line-of-sight sensing device 8, without using the automatic switching information 61, if the camera selecting mode is selected by the switching mode selecting part 72.

Moreover, the automatic switching information 61 relates to a switching timing of the camera in a single work among the works repeated by the robotic arm 1. In this embodiment, the associator 33 associates information related to the operation of the robotic arm 1 after the end effector 16 grips the assembling object W1 until it releases the gripping of the assembling object W1, with the camera selection information, to generate the automatic switching information 61. Then, when the end effector 16 releases the gripping of the assembling object W1, the automatic switching information 61 is stored in the storage device 6.

Since the robotic arm 1 operates by manually operating the remote control device 2, the robotic arm 1 may operate differently in many cases in each of the repeated works (e.g., tracing different routes). Thus, even if the operation of the robotic arm 1 is not completely in the same operating state as that when the line-of-sight sensing device 8 switches the captured image on the main monitor 50, the associator 33 generates the automatic switching information so that the captured image on the main monitor 50 is switched automatically when it becomes substantially the same operating state. For example, even if the position of the tip-end part of the robotic arm 1 is not the completely same position as that when the line-of-sight sensing device 8 switches the captured image on the main monitor 50, the associator 33 may generate the automatic switching information so that the captured image on the main monitor 50 is switched automatically when it becomes substantially the same position. More specifically, the associator 33 may generate the automatic switching information so that the captured image on the main monitor 50 is switched automatically when the position of the tip-end part of the robotic arm 1 moves within a given distance range from the position when the line-of-sight sensing device 8 switches the captured image on the main monitor 50.

Next, the image switching processing by the image processor 32 is described. As described above, the processing mode of the image processor 32 is able to take, by operating the switching mode selecting part 72, the camera selecting mode in which the captured image displayed on the main monitor 50 is switched by the operator's selection, or the automatic switching mode in which the captured image displayed on the main monitor 50 is switched automatically. Note that, when no automatic switching information 61 is stored in the storage device 6, the camera selecting mode is automatically selected as the processing mode of the image processor 32.

When the camera selecting mode is selected by the switching mode selecting part 72, the image processor 32 switches the captured image displayed on the main monitor 50 by using the camera selection information sent from the line-of-sight sensing device 8. Specifically, in a case where the camera selecting mode is selected by the switching mode selecting part 72, the image processor 32 sends to the main monitor 50 the captured image from the camera selected from the first to fourth cameras 41-44 based on the camera selection information when the camera selection information is sent from the line-of-sight sensing device 8.

That is, when the camera selecting mode is selected by the switching mode selecting part 72, the operator manipulates the remote control device 2 while suitably switching the captured image displayed on the main monitor 50 by the line-of-sight sensing device 8 so that the robotic arm 1 performs the assembling work. Moreover, once the robotic arm 1 finishes one assembling work in the state where the camera selecting mode is selected by the switching mode selecting part 72, the automatic switching information 61 is stored in the storage device 6.

Also in subsequent assembling works, the automatic switching information 61 is stored in the storage device 6 every time the robotic arm 1 finishes one assembling work, while the camera selecting mode is selected by the switching mode selecting part 72. In this embodiment, the automatic switching information 61 stored in the storage device 6 increases each time the robotic arm 1 finishes the assembling work. Note that, for example, the automatic switching information 61 generated when the robotic arm 1 finishes the assembling work may be stored in the storage device 6 so as to overwrite the automatic switching information 61 stored for the previous work.

When the automatic switching mode is selected by the switching mode selecting part 72, the image processor 32 switches the captured image displayed on the main monitor 50 by using the automatic switching information 61 stored in the storage device 6. Specifically, when the automatic switching mode is selected by the switching mode selecting part 72, the image processor 32 sends to the main monitor 50 the captured image from the camera selected from the first to fourth cameras 41-44 based on the automatic switching information stored in the storage device 6.

In this embodiment, when a plurality of automatic switching information 61 are stored in the storage device 6, the automatic switching information generator 34 is capable of generating new automatic switching information 61 by using the plurality of automatic switching information 61 stored in the storage device 6. Then, the image processor 32 is capable of sending to the main monitor 50 the captured image from the camera selected based on the automatic switching information 61 generated by the automatic switching information generator 34. The method of generating the new automatic switching information 61 by the automatic switching information generator 34 is not limited in particular, but an algorithm which makes the switching timing of the captured image more suitable may be adopted. For example, the automatic switching information generator 34 may extract coordinates of the tip-end part of the robotic arm 1 from the plurality of automatic switching information 61 stored in the storage device 6 when switching from one certain camera (e.g., the first camera 41) to another camera (e.g., the second camera 42), and may calculate coordinates which is averages of the extracted coordinates, an error of the extracted coordinates from the average coordinates, or the like. Then, based on the calculated values, the new automatic switching information 61 may be generated.

As described above, in the robot system 100 according to this embodiment, one camera among the first to fourth cameras 41-44 is selected by the line-of-sight sensing device 8 as the camera selecting device, and the captured image displayed on the main monitor 50 is switched. Moreover, the information where the operational information related to the operation on the robotic arm 1 in the work is associated with the camera selection information is stored in the storage device 6 as the automatic switching information 61. Thus, in the subsequent works of the robotic arm 1, even if the camera selection is not made by the line-of-sight sensing device 8, the image processor 32 is capable of automatically switching the captured image displayed on the main monitor 50 based on the automatic switching information 61 stored in the storage device 6 so that the captured image is suitable for remotely manipulating the robotic arm 1. Further, since the automatic switching information 61 is storable in actual work by performing the camera switching by using the line-of-sight sensing device 8, the timing of automatically switching the camera can be adjusted in the real work even if the timing of the camera switching is not preadjusted before the work.

Moreover, in this embodiment, it can be selected whether the captured image displayed on the main monitor 50 is switched by the operator's selection by using the switching mode selecting part 72, or switched automatically. Thus, the operator is able to change the method of switching the camera flexibly according to the contents of work, the work object, etc.

Moreover, in this embodiment, the line-of-sight sensing device 8 which senses the operator's line-of-sight is used as a means for an operator to select the camera. Thus, the selection of the camera for switching the image of the main monitor 50 can be performed without using hands. Moreover, the line-of-sight sensing device 8 senses the operator's line-of-sight to identify the sub-monitor to which the operator's line-of-sight is directed for the given period of time, and accepts the camera corresponding to the identified sub-monitor as the camera selected by the operator. Thus, the operator is able to check the captured image displayed on each sub-monitor before switching the captured image of the main monitor 50.

Moreover, in this embodiment, when the plurality of automatic switching information 61 are stored in the storage device 6, the automatic switching information generator 34 is capable of generating the automatic switching information 61 which offers the more suitable timing of switching the camera by using the plurality of automatic switching information 61 stored in the storage device 6.

Second Embodiment

Figure 3:
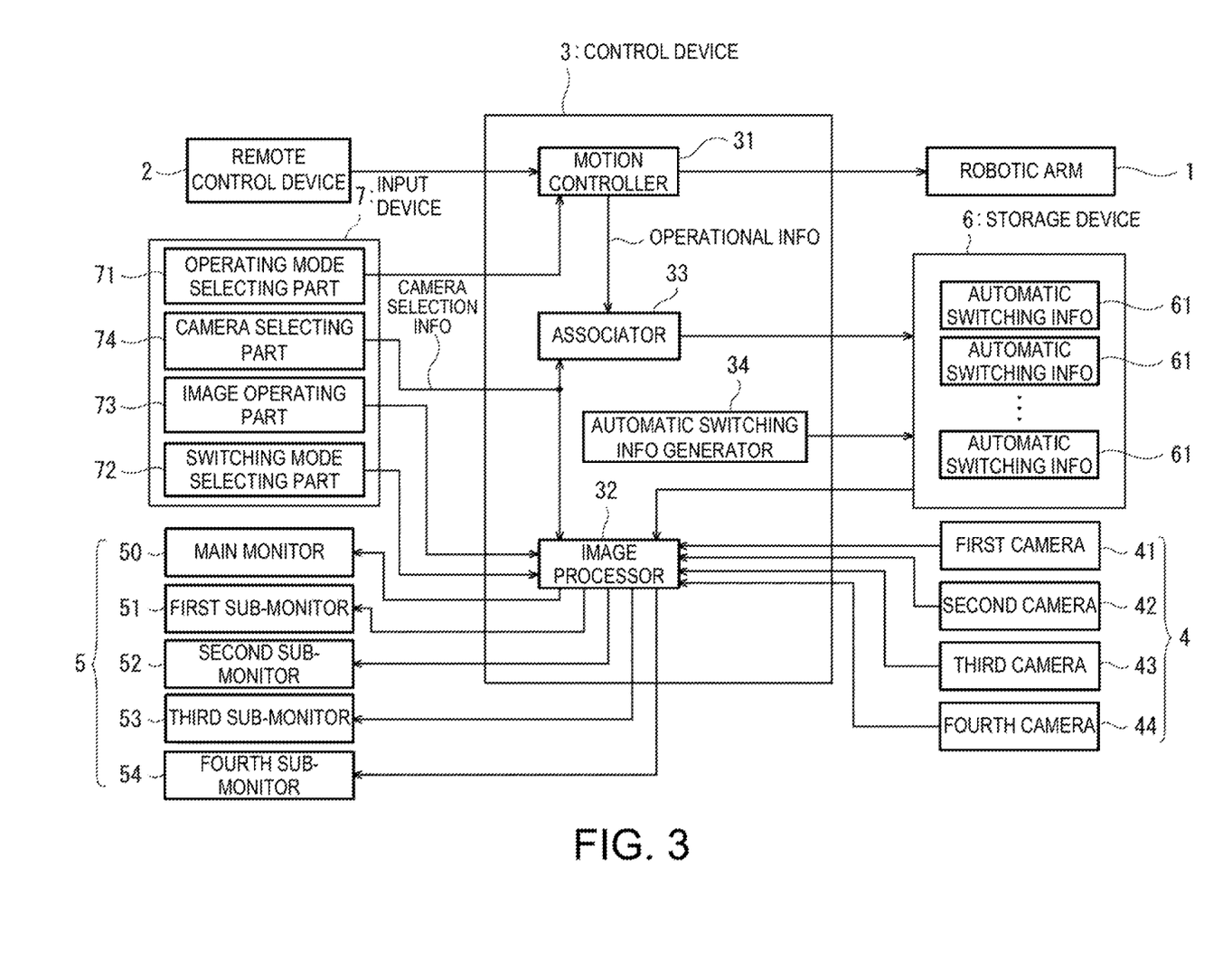
FIG. 3 is a schematic diagram illustrating a configuration of a control system of a remote control robot system according to a second embodiment.

Next, with reference to FIG. 3, a remote control robot system according to a second embodiment is described. Note that, in this embodiment, the same reference characters are given to the same component as the first embodiment to omit redundant description.

FIG. 3 is a schematic diagram illustrating a configuration of a control system of the remote control robot system according to the second embodiment. In this embodiment, the system is provided with a camera selecting part 74 by which the input device 7 functions as the camera selecting device, instead of the line-of-sight sensing device 8 of the first embodiment. Also in this embodiment, although the input device 7 is a tablet terminal, it is not limited to this configuration, similar to the first embodiment. The camera selecting part 74 receives a selection of one camera from the first to fourth cameras 41-44 by a manual operation from an operator. Then, the camera selecting part 74 generates the camera selection information, and sends it to the image processor 32 and the associator 33 of the control device 3.

In this embodiment, the first to fourth sub-monitors 51-54 are used in order for the operator to check the captured images which are imaged by the first to fourth cameras 41-44. That is, the operator manipulates the remote control device 2 while looking at the captured image displayed on the main monitor 50. The operator suitably checks the captured images on the first to fourth sub-monitors 51-54, and operates the camera selecting part 74 to switch the captured image displayed on the main monitor 50. Instead of the first to fourth sub-monitors 51-54, the four captured images from the first to fourth cameras 41-44 may be displayed on a single sub-monitor.

Also in this embodiment, similar effects to the first embodiment can be acquired.

OTHER EMBODIMENTS

The present disclosure is not limited to the embodiments described above, and various modifications may be possible without departing from the spirit of the present disclosure.

For example, in the embodiments described above, although the remote control device 2 is the joystick, it is not limited in particular, and for example, the remote control device 2 may be a master arm which is manually operated.

In the embodiments described above, although the respective input parts 71-74, such as the operating mode selecting part 71 and the switching mode selecting part 72, are provided to the single input device 7, they may be provided to separate input devices. Moreover, the remote control device 2 and the input device 7 may be configured integrally. Moreover, in the embodiments described above, although the motion controller 31 and the image processor 32 are provided to the single control device 3, the motion controller 31 and the image processor 32 may be provided to separate control devices.

Moreover, in the embodiments described above, although the operator is able to select from the automatic mode, the correctable automatic mode, and the manual mode as the operating mode in which the robotic arm 1 is operated, the operating mode in which the robotic arm 1 is operated may include at least one of the manual mode and the correctable automatic mode.

Moreover, in the embodiments described above, when the plurality of automatic switching information 61 are stored in the storage device 6, the image processor 32 sends to the main monitor 50 the captured image from the camera selected based on the automatic switching information 61 generated by the automatic switching information generator 34, but it is not limited to this configuration. For example, the image processor 32 may be configured to send to the main monitor 50 the captured image from the camera selected based on the newest automatic switching information 61 among the plurality of automatic switching information 61 stored in the storage device 6. Alternatively, the image processor 32 may be configured to send to the main monitor 50 the captured image from the camera selected based on the newest automatic switching information 61 among the plurality of automatic switching information 61 stored in the storage device 6. For example, the input device 7 may select the automatic switching information used in the image processor 32 from the plurality of automatic switching information 61 stored in the storage device 6. In these cases, the control device 3 may not be provided with the automatic switching information generator 34.

Moreover, in the embodiments described above, although the cameras 41, 43 and 44 other than the second camera 42 fixed to the robotic arm 1 are provided so that their relative positions with respect to the assembled object W2 are fixed, the relative positions with respect to the assembled object W2 may be configured to be changed. For example, the camera may be configured approachable to the assembled object W2. For example, when the industrial robot 10 is a robot which performs a paint work, the camera may be configured to approach the assembled object W2 when positioning a paint gun which is the end effector 16, and separate from the assembled object W2 when spraying paint from the paint gun so that it does not get dirty with the paint.

DESCRIPTION OF REFERENCE CHARACTERS

1 Robotic Arm
16 End Effector
2 Remote Control Device
33 Image Processor
41 First Camera
42 Second Camera
43 Third Camera
44 Fourth Camera
50 Main Monitor (Monitor)
51 First Sub-monitor (Sub-monitor)
52 Second Sub-monitor (Sub-monitor)
53 Third Sub-monitor (Sub-monitor)
54 Fourth Sub-monitor (Sub-monitor)
6 Storage Device
61 Automatic Switching Information
71 Operating Mode Selecting Part
72 Switching Mode Selecting Part
8 Line-of-sight Sensing Device (Camera Selecting Device)
100 Remote Control Robot System

What is claimed is:

1. A remote control robot system, comprising:
a robotic arm configured to perform a given work, the robotic arm having an end effector at a tip-end part of the robotic arm;
a remote control device for an operator to remotely manipulate operation of the robotic arm;
a plurality of cameras configured to image the work of the robotic arm;
a monitor configured to display a captured image that is sent from at least one of the plurality of cameras;
a camera selecting device configured to generate, in response to receiving an operator's selection of one camera from the plurality of cameras, camera selection information for switching the captured image displayed on the monitor, the switching being such that a captured image from a first camera among the plurality of cameras is switched to a captured image from a camera other than the first camera among the plurality of cameras;
a storage device configured to store information where operational information related to operation of the robotic arm in the work is associated with the camera selection information, as automatic switching information for automatically performing the switching of the captured image on the monitor according to the operation of the robotic arm which is represented by the operational information, the operational information being one or more of positional information on the tip-end part of the robotic arm and posture information on the robotic arm; and
an image processor configured to automatically perform the switching of the captured image displayed on the monitor by using the automatic switching information stored in the storage device, wherein the image processor is configured to send to the monitor the captured image from the camera selected from the plurality of cameras based on the automatic switching information.

2. The remote control robot system of claim 1, further comprising a switching mode selecting part configured to receive an operator's selection of one of a camera selecting mode in which the captured image from the camera selected based on the camera selection information sent from the camera selecting device is sent to the monitor, and an automatic switching mode in which the captured image from the camera selected based on the automatic switching information stored in the storage device is sent to the monitor, as a processing mode of the image processor.

3. The remote control robot system of claim 1, comprising a plurality of sub-monitors, different from the monitor, provided corresponding to the plurality of cameras, respectively, and configured to display the captured images from the corresponding cameras among the plurality of cameras,
wherein the camera selecting device senses an operator's line-of-sight to identify the sub-monitor among the plurality of sub-monitors, to which the operator's line-of-sight is directed for a given period of time, and accepts the camera corresponding to the identified sub-monitor as the camera selected by the operator.

4. The remote control robot system of claim 2, comprising a plurality of sub-monitors, different from the monitor, provided corresponding to the plurality of cameras, respectively, and configured to display the captured images from the corresponding cameras among the plurality of cameras,
wherein the camera selecting device senses an operator's line-of-sight to identify the sub-monitor among the plurality of sub-monitors, to which the operator's line-of-sight is directed for a given period of time, and accepts the camera corresponding to the identified sub-monitor as the camera selected by the operator.

* * * * *